United States Patent [19]

Petrie et al.

[11] Patent Number: 5,533,206
[45] Date of Patent: Jul. 9, 1996

[54] WELDING HELMET WITH REMOVABLE ELECTRONIC QUICK CHANGE CARTRIDGE

[75] Inventors: Michael J. Petrie, Walker; Daniel A. Pleune, Rockford, both of Mich.

[73] Assignee: Jackson Products, Inc., Belmont, Mich.

[21] Appl. No.: 518,144

[22] Filed: Aug. 23, 1995

[51] Int. Cl.⁶ .................................................. A61F 9/06
[52] U.S. Cl. ................................................................ 2/8
[58] Field of Search .......................... 2/7, 8, 9, 10, 422, 2/424, 427, 429, 906; 219/147

[56] References Cited

U.S. PATENT DOCUMENTS

| | | | |
|---|---|---|---|
| Re. 29,684 | 6/1978 | Gordon | 219/147 |
| 3,112,490 | 12/1963 | Malcom, Jr. | 2/8 |
| 3,212,101 | 10/1965 | Benner | 2/8 |
| 3,440,661 | 4/1969 | Newcomb | 2/8 |
| 3,577,563 | 5/1971 | Raschke | 2/8 |
| 4,774,723 | 10/1988 | Ruck | 2/8 |
| 4,863,244 | 9/1989 | Fuerthbauer et al. | 350/332 |
| 5,062,156 | 11/1991 | Siegal | 2/8 |

Primary Examiner—Michael A. Neas
Attorney, Agent, or Firm—Edward H. Renner

[57] ABSTRACT

Within a welding helmet, an easily removable electronic quick change ("EQC") cartridge is retained into an integral cartridge housing. The EQC cartridge has slots on its top which can accommodate flanges from the housing, and tabs on its sides for insertion into slots of the housing. The tabs are located on the ends of an elastic spring bar which is inside the EQC cartridge. Switches connected to the spring bar by an elevated support lie above the EQC cartridge, which when compressed internalize the tabs inside the cartridge. When the EQC cartridge is positioned within the housing, the switches are released and the tabs extend through the slots of the housing.

12 Claims, 3 Drawing Sheets

WELDING HELMET WITH REMOVABLE ELECTRONIC QUICK CHANGE CARTRIDGE

BACKGROUND OF THE INVENTION

1. Field of the Invention

The present invention relates to welding helmet technology, and more particularly to the retention of removable eye shields or electronic quick change ("CQC") cartridges within a welding helmet.

2. Description of Related Art

Traditionally, welding helmets had darkened lenses which protected the user's eyes from the intense light caused by sparks discharged during welding. The intense light, without such protection, could cause serious injuries to the welder such as retinal burnout. However, because the lenses were unduly dark, the lenses had to be raised away from the user's eyes when the user needed light to see his or her work, and lowered during welding. Consequently, the helmets did not provide sufficient protection to the user because the lenses did not provide continuous eye protection, which was particularly critical in emergency situations.

The manual raising or lowering of the eyepiece was eliminated by the use of the liquid crystal display ("LCD") lens, as characterized by U.S. Pat. No. Re. 29,684 Gordon. The '684 patent teaches a fixed position LCD lens comprising a layer of liquid crystal material enclosed between two opposing parallel plates coated with transparent conducting films. The liquid crystal material is arranged such that when a suitable electrical potential is established across the conducting films and the liquid crystal layer, the lens assembly changes from a uniform light transmitting condition to a uniform eye protecting approximately opaque condition. Thus, as the welder creates a spark, the liquid crystal changes from the light transmitting condition to the eye protecting condition. A shortcoming of the '684 Patent, however, is that the LCD lens cannot be removed from the helmet such as needed when the lens becomes damaged or otherwise.

An EQC cartridge is a device which has an adjustable LCD lens that can be removed from the helmet. In the prior art, the EQC cartridge is electrically coupled to a source in the helmet, whereby the operator can manually adjust the light transmittancy through the lens. The EQC cartridge is held into place on the helmet by a spring cartridge. To install the spring cartridge, the EQC cartridge is placed onto the helmet and the spring cartridge is thereafter placed around the EQC cartridge. However, in addition to requiring an extra part, i.e. the spring cartridge, the installation and removal of the EQC cartridge with the spring cartridge is extremely cumbersome.

A face shield filter plate retainer for welding helmets that does not employ spring cartridges or other additional parts is taught by U.S. Pat. No. 5,062,116 Siegal. The '116 patent discloses a face-protecting device that includes a filter plate retained on a support ledge on the exterior of the helmet by means of a flexible filter plate retainer provided with integral fastening means that protect inwardly therefrom. The retainer, however, mounts the lens to the front of the helmet, which is inadequate for use with an EQC cartridge. An EQC cartridge with its intricate controls is extremely expensive and thus requires protection within the helmet. Furthermore, it is inconvenient for the user to have to remove the helmet and rotate it to adjust the controls.

With the above considerations in mind, an object of the present invention is to provide a system for retaining an EQC cartridge within a welding helmet which eliminates the spring cartridge that currently holds the EQC cartridge in place.

It is a further object of the invention to provide a retention system in which the EQC cartridge is easily installable and removable due to damage or inoperateness.

Finally, it is still another further object of this invention to provide a retention system in which the EQC cartridge is attached to the helmet from the inside to protect the EQC cartridge electronics from external hazards and to facilitate the adjustment of the controls by the user.

SUMMARY OF THE INVENTION

The present invention is a welding helmet that releasably retains an EQC cartridge having an adjustable LCD lens. The helmet includes a frame-shaped cartridge housing that includes flanges on its top and a slot on each of its sides. The EQC cartridge has slots on its top side to receive the flanges of the cartridge housing, and a tab located on each side for removable insertion into the slots of the housing.

Because the tabs extend beyond the width of the housing during insertion, the EQC cartridge can only be inserted by inwardly pressing a pair of coupled switches, each of which is located on a side of the EQC cartridge. The pressing of the switches compresses an elastic bar which has the tabs situated on its ends and is located inside the EQC cartridge. The tabs internalize so that the EQC cartridge can be positioned within the housing. When this is accomplished, the switches are released and the tabs are inserted into the slots on the housing. The EQC cartridge is then secured to the inside of the welding helmet.

BRIEF DESCRIPTION OF THE DRAWINGS

The above-mentioned and other features, advantages and objects of this invention, in the manner in which they are obtained, will become more apparent and will be best understood by reference to the detailed description in conjunction with the accompanying drawings which follow, wherein.

DESCRIPTION OF THE PREFERRED EMBODIMENTS

Figure 1:
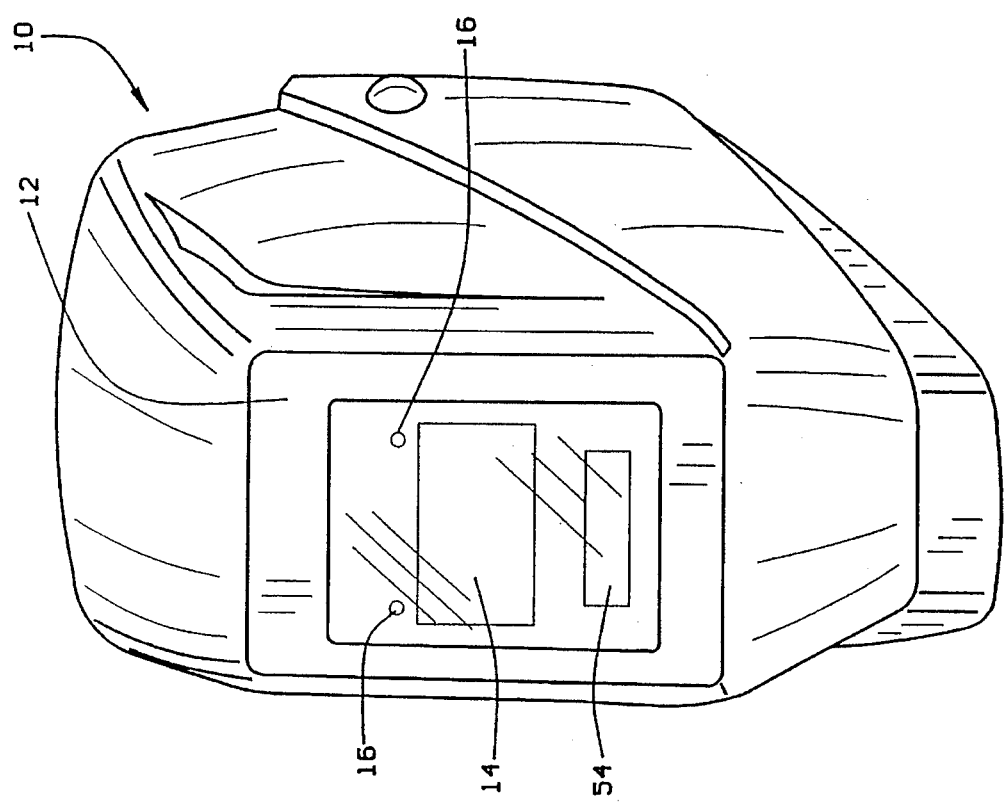
FIG. 1 is a perspective view of the welding helmet of the present invention.

Referring to FIG. 1, a welding helmet 10 is shown incorporating an EQC cartridge 12. The EQC cartridge 12 includes an LCD lens 14, solar cells 54 and photo sensor cells 16 on its front side or face. The EQC cartridge 12 is positioned on the front side of the welding helmet 10 so that the LCD lens 14 is positioned directly in front of the eyes of the wearer, thereby functioning as the actual viewing window. The solar cells 54 absorb light and function as the energy input for a topical recharging circuit (not shown) for the batteries 20 (shown in FIG. 3) which are accessible by a battery cover 21. The photo sensor cells 16 detect sparks and other intense light and act as the input to a circuit (not shown) that automatically adjusts the LCD lens 14 to a variable opaque condition. Although the welding helmet 10 is shown having a narrow shell design, it is understood that the invention can be adapted to helmets of various shapes and sizes.

Figure 3:
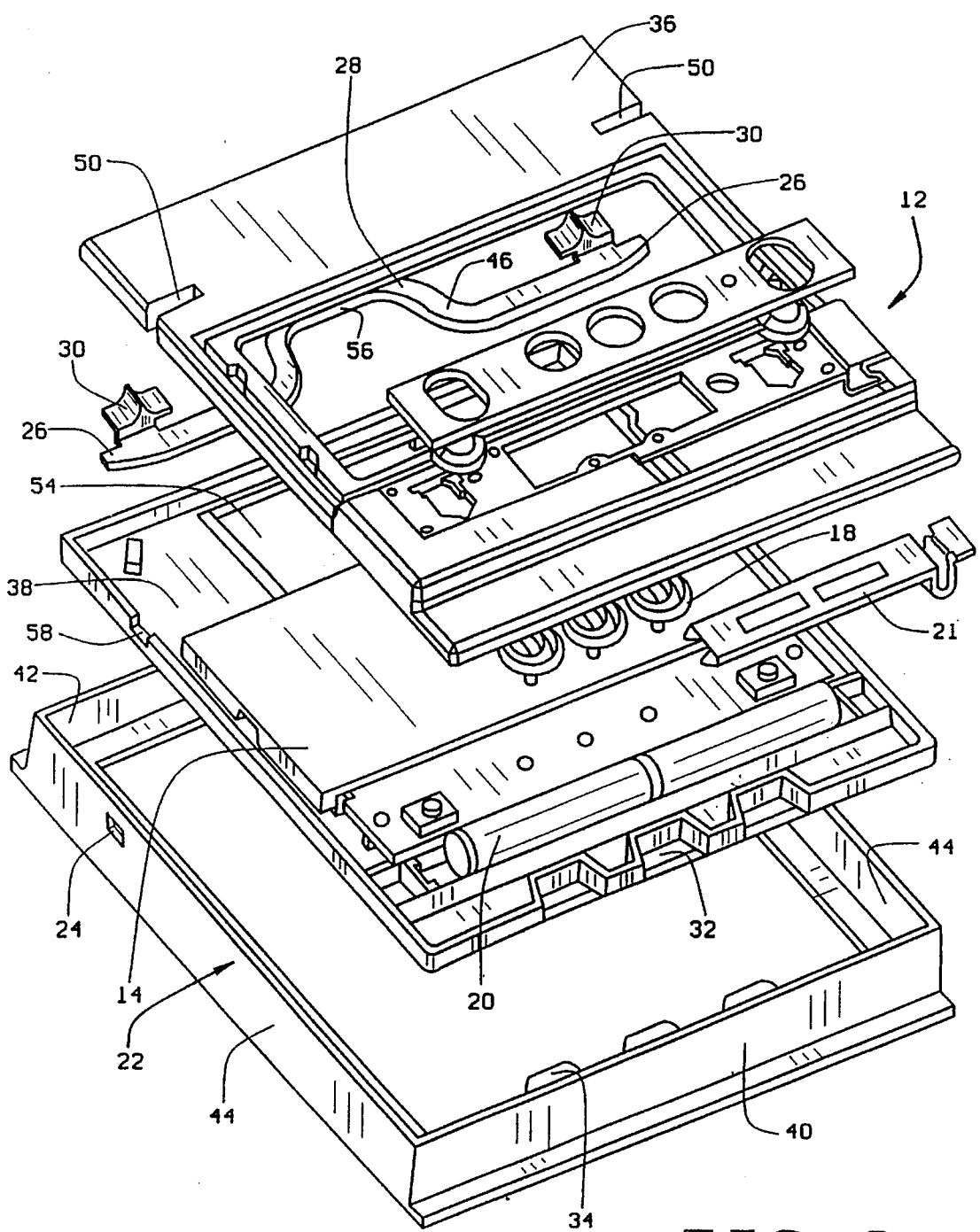
FIG. 3 is an enlarged perspective view of the cartridge housing and a dissembled EQC cartridge of the present invention.

As illustrated in FIG. 3, the EQC cartridge 12 generally consists of a cover 36 and a base 38. The solar cells 54 and the photo sensor cells 16 are located inside the cartridge. The solar cells 54 can be seen in FIG. 3. The photo sensor cells 16 are on an opposite side of the circuit board, and therefore, cannot be seen. The LCD lens 14 is positioned between the cover 36 and the base 38. As typical in the art, the LCD lens 14 is either darkened or transparent depending on whether or not a specific voltage is applied to it. The LCD lens 14 can also be manually variably controlled by the user, such as for individual sensitivity to the amount of light passing through the LCD lens 14, by adjusting the control knobs 18.

Figure 4:
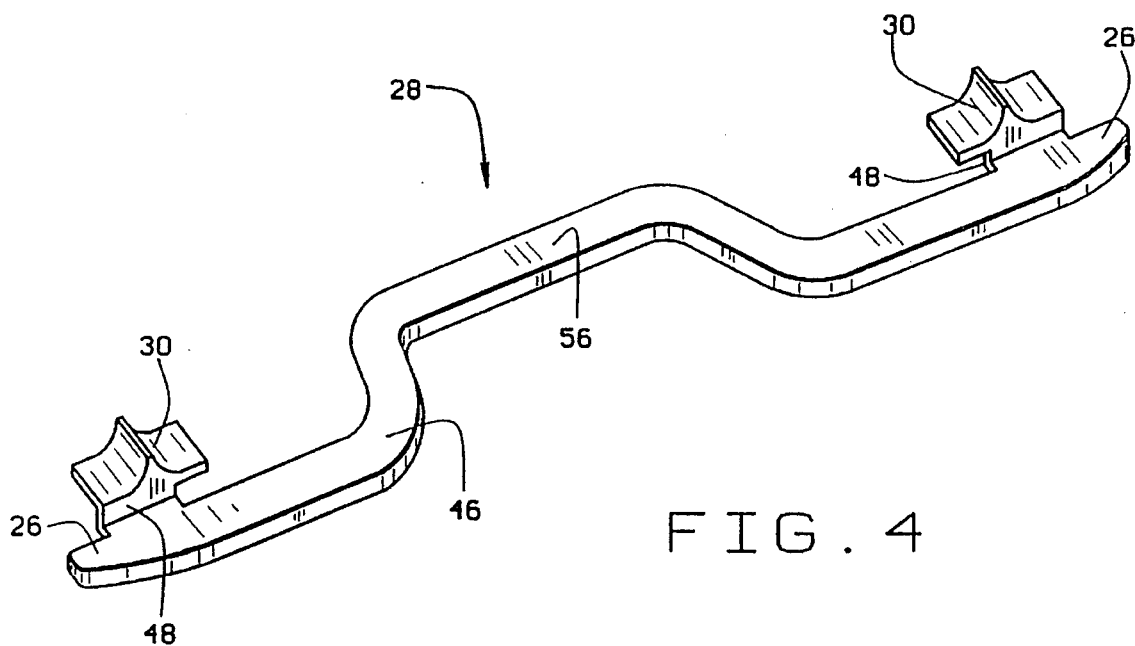
FIG. 4 is an enlarged perspective view of the spring bar of the EQC cartridge of FIG. 3.
Figure 5:
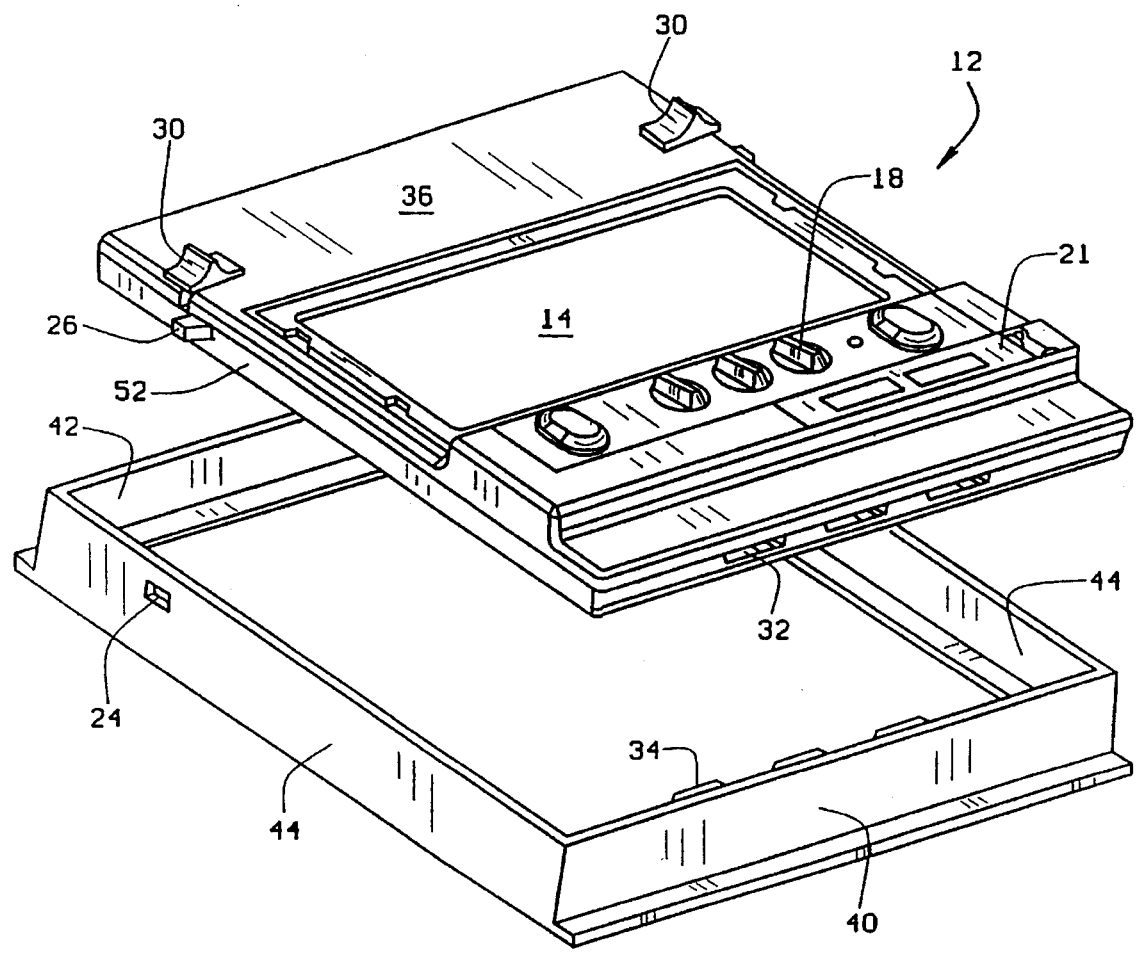
FIG. 5 is an enlarged perspective view of the cartridge housing and the EQC cartridge of the present invention.

A spring bar 28 is located inside the EQC cartridge 12, as best illustrated in FIGS. 3 and 4. The spring bar 28 is made of an elastic material, such as plastic, and generally comprises a U-shaped member 56 with extending side projections 46. Each projection 46 has a switch 30 located a short distance from the end of the projection 46, which is elevated from the spring bar 28 by means of a vertical support 48. A pair of tabs 26 extend beyond the switches 30, and form the ends of the projections 46.

The cover 36 of the EQC cartridge 12 has a pair of horizontal slits 50 and the base 38 has a pair of cavities 58, so that when the spring bar 28 is placed within the cover 36 and the base 38 the switches 30 lie above the slits 50 on the cover 36 and the tabs 26 extend from the sides 52 through the cavities 58 of the base 38.

Figure 2:
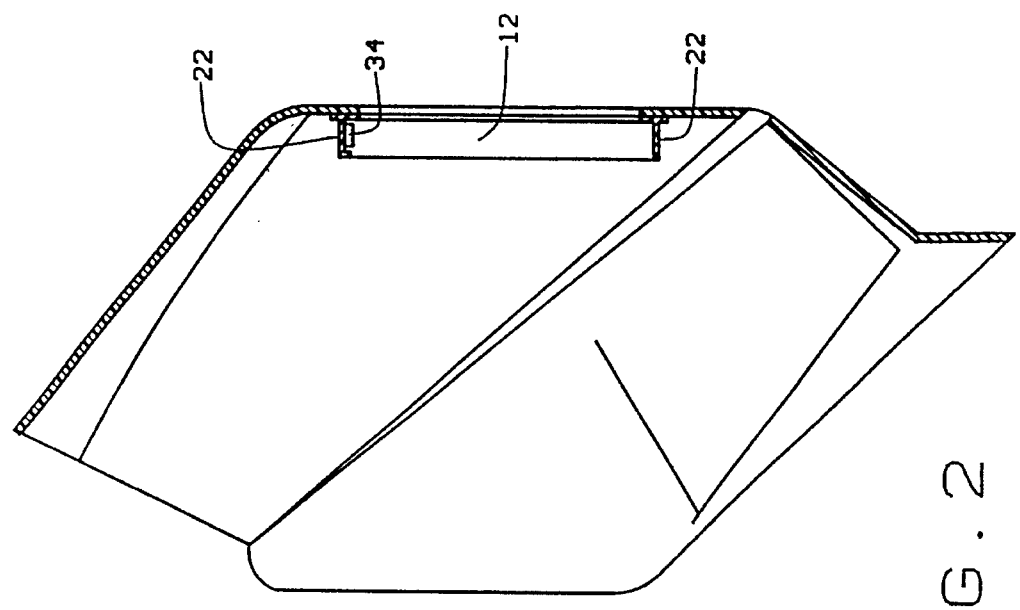
FIG. 2 is a cross-sectional view of the welding helmet of FIG. 1, showing an EQC cartridge retained by an integral cartridge housing.

A cartridge housing 22 retains the EQC cartridge 12 within the helmet 10, as best depicted in FIG. 2. The housing 22 is in the form of a frame with a top 40, a bottom 42, and sides 44. The housing 22 has three flanges 34 on its top 40, and a slot 24 on each of its sides 44. The housing 22 may be integral with the helmet.

For insertion of the EQC cartridge 12 into the cartridge housing 22, the flanges 34 of the cartridge housing 22 are positioned into the slots 32 of the EQC cartridge 12. Because the tabs 26 extend beyond the sides 44 of the housing 22, the switches 30 on the EQC cartridge 12 are pushed inward, thereby internalizing the tabs 26 within the EQC cartridge 12. The EQC cartridge 12 is then positioned inside the cartridge housing 22, and the switches 30 are released. The tabs 26 externalize and extend through the slots 24 on the sides 44 of the housing 22. The EQC cartridge 12 is then secured into place. To remove the EQC cartridge 12, the reverse procedure is followed.

It should be understood that the cartridge 12 may include tabs rather than slots while the housing 22 may have slots rather than tabs.

Also, the tabs and slots may be oppositely disposed on the housing and cartridge than that indicated herein without sacrificing performance or otherwise.

Accordingly, while this invention is described with reference to preferred embodiments of the invention, it is not intended to be construed in a limiting sense. It is rather intended to cover any variations, uses or adaptations in the invention utilizing its general principles. Various modifications will be apparent to persons skilled in the art upon reference to this description. It is therefore contemplated that the appended claims will cover any such modifications or embodiments as fall within the true scope of the invention.

What is claimed is:

1. A welding helmet, including:
   a) an electronic quick change cartridge having a base and a cover, said cartridge including a liquid crystal display lens disposed between said base and said cover, said cartridge further having a plurality of slots on a side;
   b) a spring bar positioned inside said cartridge having a U-shaped member with a pair of side projections extending therefrom, each of said projections having a tab on the end of said projection and further having a switch suspended from a support bracket between said U-shaped member and said tab; and
   c) a cartridge housing in the form of a frame located inside of said helmet for retaining said cartridge within said helmet, said housing having a plurality of flanges on a side of said housing to insert into said slots on said cartridge, said housing further including a pair of slots, each of said slots located on opposite sides of said housing for receiving said tabs of said spring bar.

2. The welding helmet of claim 1, wherein said side with said plurality of slots of said cartridge is the top side, and said side with said plurality of flanges on said housing is the top side.

3. The welding helmet of claim 1, wherein said spring bar is made of an elastic material.

4. The welding helmet of claim 3, wherein said elastic material is plastic.

5. In a welding hood having a rectangular opening in the front, a device for releasably retaining an electronic quick change cartridge adjacent the opening, the device comprising:
   a) a rectangular frame disposed on an inside of the hood surrounding the opening, said frame including first retention means on a top side of said frame for holding the electronic quick change cartridge within the frame, and a pair of slots one on both lateral sides of said frame relative said top side; and
   b) the electronic quick change cartridge having second retention means at a top side of the cartridge for holding the electronic quick change cartridge within the frame, said second retention means cooperating with said first retention means to retain the top of the electronic quick change cartridge within said frame adjacent to the opening, said electronic quick change cartridge further having a resilient spring arm with two ends, each end terminating with a tab adapted to be received in a respective said frame slot, said spring arm further including an integral knob adjacent each tab for grasping by a user in order to extend and retract said tabs such that when said tabs are extended said tabs are received in said frame slots to hold the electronic quick change cartridge within said frame, and when said tabs are retracted the cartridge may be removed.

6. The welding hood of claim 5, wherein said frame is formed integral with the hood.

7. The welding hood of claim 5, wherein said first retention means is a plurality of slots and said second retention means is a plurality of tabs corresponding in number to said plurality of slots.

8. The welding hood of claim 7, wherein said plurality of slots is three.

9. The welding hood of claim 5, wherein said first retention means is a plurality of tabs and said second retention means is a plurality of slots corresponding in number to said plurality of tabs.

10. The welding hood of claim 9, wherein said plurality of tabs is three.

11. The welding hood of claim 5, wherein said spring arm is made of a plastic.

12. A method of releasably retaining an electronic quick change cartridge within a welding hood adjacent an opening in the front of the hood, the method comprising the steps of:

a) providing a frame on the inside of and integral to the hood adjacent and surrounding the opening;

b) providing a tab on a top side of said frame;

c) providing a slot on each lateral side of said frame relative to said top side;

d) providing a resilient member on the electronic quick change cartridge that has two tabs adapted to be retractably received by respective said slots on said lateral sides of said frame;

e) providing a slot on the top of the electronic quick change cartridge; and f) inserting the slot of the electronic quick change cartridge into said tab of said frame, and said tabs of said resilient member into said slots on said lateral sides of said frame, thereby holding the electronic quick change cartridge within said frame.

\* \* \* \* \*